United States Patent [19]
Spina

[11] Patent Number: 5,273,157
[45] Date of Patent: Dec. 28, 1993

[54] HANDLE FOR SURGERY LAMP
[75] Inventor: Charles Spina, Ross, Calif.
[73] Assignee: MDT Corporation, Torrance, Calif.
[21] Appl. No.: 633,228
[22] Filed: Dec. 13, 1990

Related U.S. Application Data
[63] Continuation of Ser. No. 164,333, Mar. 4, 1988.
[51] Int. Cl.⁵ .............................................. B65D 69/00
[52] U.S. Cl. ................................... 206/223; 206/438; 16/114 R; 362/804
[58] Field of Search ...................... 206/223, 438, 439; 362/269, 285, 804, 109; 16/114 R, 114 A, DIG. 24

[56] References Cited
U.S. PATENT DOCUMENTS

| | | |
|---|---|---|
| D. 289,206 | 4/1987 | Scoville et al. . |
| D. 298,864 | 12/1988 | Jefferson ................... D26/140 |
| 135,975 | 2/1873 | Draper . |
| 1,086,676 | 2/1914 | Linscott . |
| 2,669,181 | 2/1954 | Cooper et al. . |
| 2,920,804 | 1/1960 | Minton . |
| 3,252,404 | 10/1964 | Cox . |
| 3,341,062 | 9/1967 | Phillips . |
| 4,037,096 | 7/1977 | Brendgord et al. ................ 362/294 |
| 4,135,231 | 1/1979 | Fisher . |
| 4,307,439 | 12/1981 | Sassmannshausen . |
| 4,316,237 | 2/1982 | Yamada et al. . |
| 4,365,626 | 12/1982 | House ................................. 604/192 |
| 4,402,407 | 9/1983 | Maly . |
| 4,408,692 | 10/1983 | Sigel et al. . |
| 4,538,214 | 8/1985 | Fisher et al. . |
| 4,559,042 | 12/1985 | Votel ..................................... 604/192 |
| 4,559,671 | 12/1985 | Andrews et al. .................... 362/804 |
| 4,605,124 | 8/1986 | Sandel et al. . |
| 4,742,910 | 5/1988 | Staebler ............................... 604/192 |
| 4,844,252 | 7/1989 | Barron et al. . |

FOREIGN PATENT DOCUMENTS
1072776 3/1954 France .
122643 7/1948 Sweden .

Primary Examiner—David T. Fidei
Attorney, Agent, or Firm—Trask, Britt & Rossa

[57] ABSTRACT

Handle for manipulating a lamp above an operating table including a grip portion, a connecting portion above the grip portion for connection to such lamp, said handle including radially outwardly projecting support means between the grip portion and the connecting portion, and a mountable-demountable protective disc fitted over the connecting portion and supported by the support means. Also a package of two such handles lying side by side with tie means holding them together and with a disc underlying and a disc overlying the pair of handles and secured in place.

24 Claims, 3 Drawing Sheets

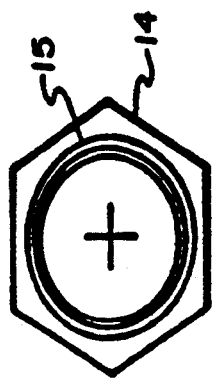
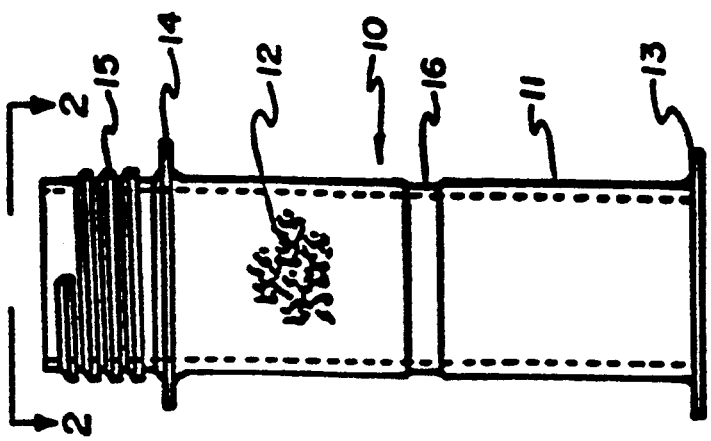
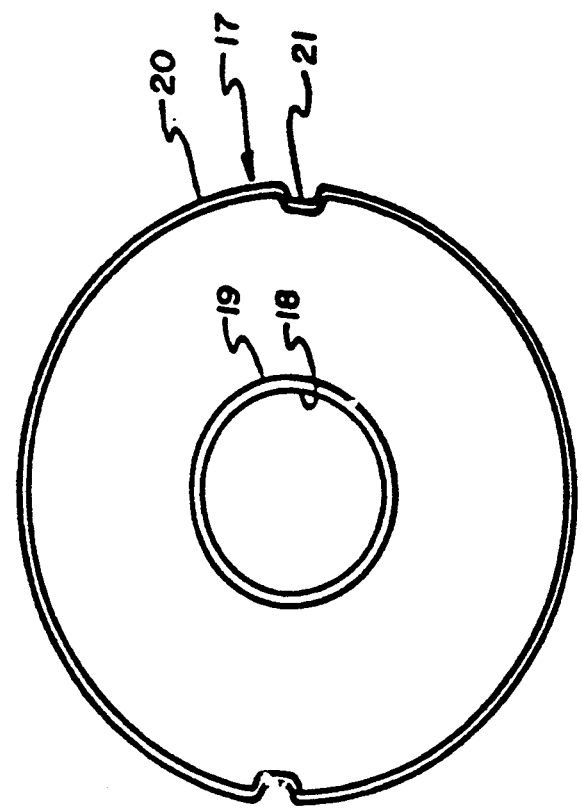

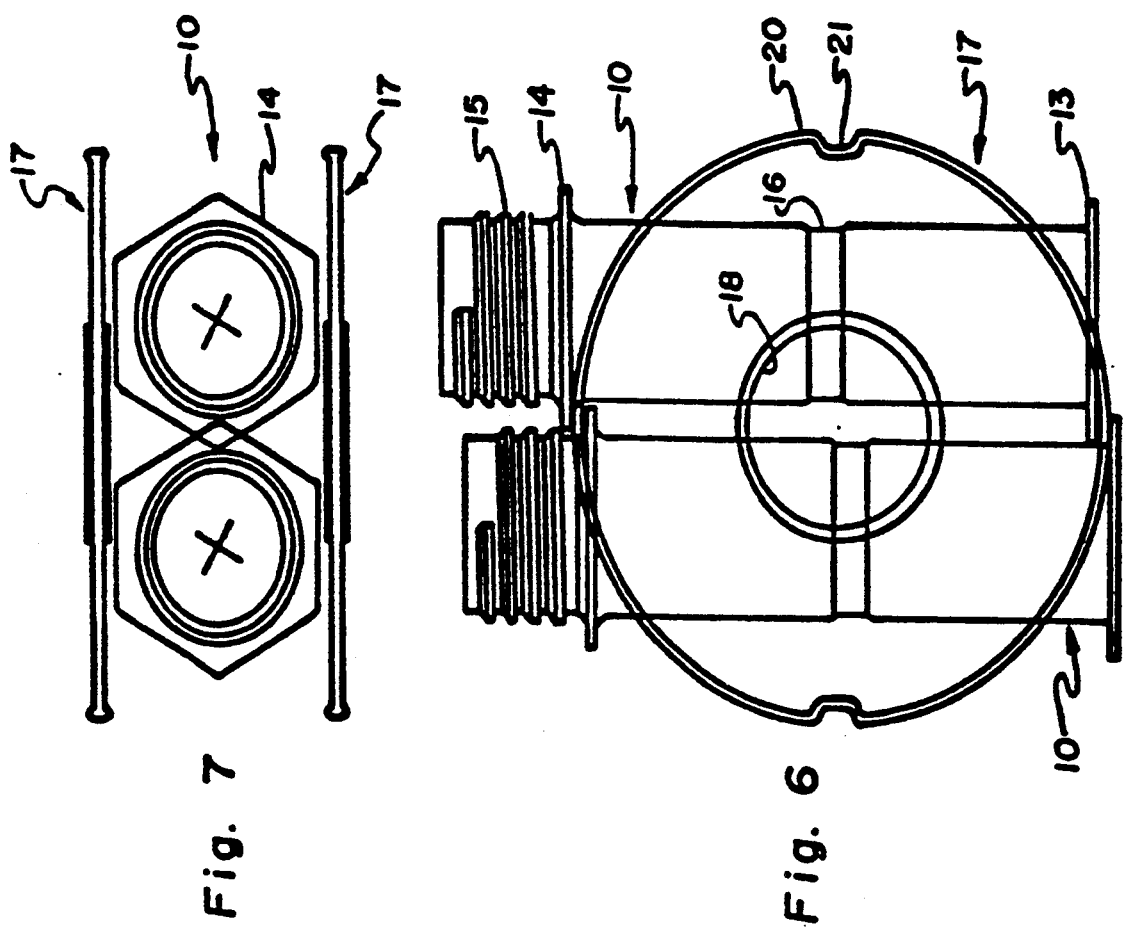

HANDLE FOR SURGERY LAMP

RELATED APPLICATIONS

This application is related to commonly assigned copending U.S. patent application Ser. No. 459,440, filed Jan. 2, 1990, titled "Handle for Surgery Lamp," and is a continuation of commonly assigned copending U.S. patent application Ser. No. 164,333 filed Mar. 4, 1988, titled "Handle for Surgery Lamp."

BACKGROUND OF THE INVENTION

1. Field

This invention relates to a novel form of handle or for use in manipulating the overhead lamp in an operating room.

2. State of the Art

During surgery it is necessary to provide overhead illumination. Such is provided by a lamp which is so mounted above the operating table that it can be manipulated to heights and positions desired. For such purpose it is common to provide a handle or grip by means of which the surgeon or others on the team can move the lamp to the desired position, the lamp being mounted so as to be moveable to any needed position, to permit vertical and lateral adjustment and to retain the lamp in any desired position until it is moved, by the handle, to another position.

In some instances the handle is a re-usable metal part of the lamp but such requires sterilization of the handle before each operation is commenced.

A disposable plastic handle is also in use which has a threaded upper portion which can be screwed into a socket on the lamp structure, or into an adaptor which is secured to the lamp structure. Below the threaded portion is a handle which is gripped by hand. As an added precaution, the handle is formed with a disc just beneath the threaded upper end which serves as a guard to prevent the gloved hand of the person manipulating the lamp from coming into contact with non-sterile parts of the lamp structure. The handle per se extends downward from the disc.

This structure is more advantageous than a metal re-usable handle because it can be packaged in sterile condition, removed from the sterile package at the time of use and then discarded.

Nevertheless, this form of detachable/attachable handle has the disadvantage that it is bulky and inconvenient to package, to ship and to store.

It is an object of the present invention to provide an attachable, detachable handle for manipulating overhead lamps used in surgery which obviates the disadvantages of handles as described above.

The above and other objects will be apparent from the ensuing description and appended claims.

BRIEF DESCRIPTION OF THE DRAWINGS

One embodiment of the invention is illustrated, by way of example, in the accompanying drawings in which FIG. 1 is a view in elevation of the handle element of the invention.

FIG. 2 is a top view as seen along the line 2—2 of FIG. 1.

FIG. 3 is a top view of a detachable, attachable disc for use with the handle of FIG. 1.

FIG. 4 is a view of the disc as seen along the line 4—4 of FIG. 3.

FIGS. 6 and 7 are, respectively, a top plan view and an end view of two handles shown with detached disks illustrating the packaging advantages of the invention.

DESCRIPTION OF THE ILLUSTRATED EMBODIMENT

Figure 5:
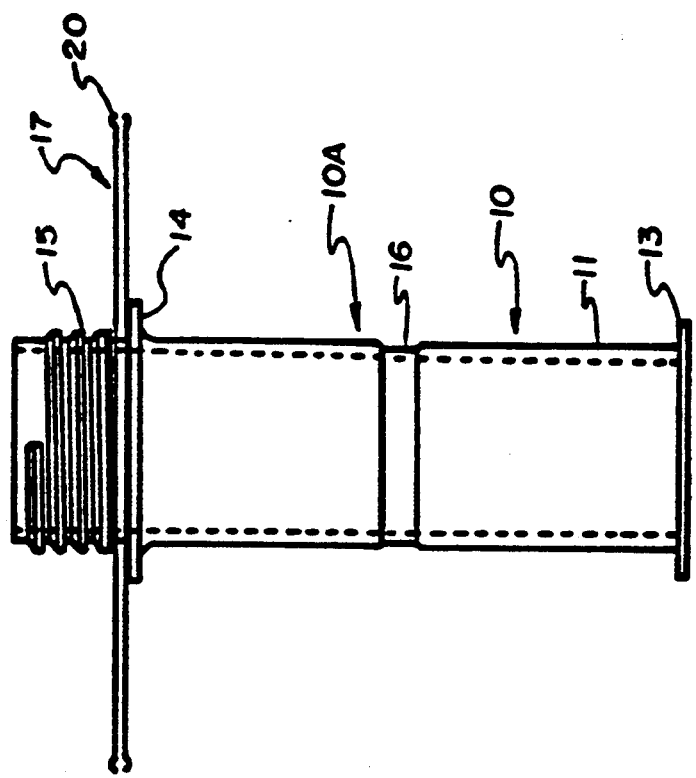
FIG. 5 is a view in elevation of the complete handle including the handle element of FIG. 1 and the disc of FIG. 3 shown mounted on the handle element.

Referring now to the drawings and initially to FIG. 1, the handle (without the protective disc) is indicated generally at 10. It is preferably molded in one piece from a suitable plastic material. It has a tubular body or handle element 11 having preferably a textured exterior 12, a flat hexagonal base 13, a hexagonal lip 14 and a threaded upper end 15 which can be screwed either into a socket (not shown) which is a part of the lamp (also not shown) or into an adapter (not shown) attached to a lamp fixture. The handle element 11 is formed about midway between base 13 and lip 14 with an annular groove 16, or alternatively with a pair of indentations.

Referring to FIGS. 3 and 4, a disc 17 is provided made, for example, of the same plastic material as the handle 10 and having a central opening 18. Surrounding the opening 18 and projecting above and below the body of the disc is an inner rim 19. An outer rim 20 projects above and below the disc. Notches 21 are provided at opposite ends of a diameter of the disc.

Referring now to FIG. 5, the complete assembly, indicated as 10A, has the disc 17 mounted on the lip 14, the hole 18 being such that the disc fits snugly over the threaded portion 15, the fit being such that the disc is stable but not difficult to place it in and to remove it from the position shown in FIG. 5.

Referring now to FIGS. 6 and 7, a pair of the handles 10 and discs 17 are packaged as shown. The handles 10 are laid alongside one another but slightly offset so that the bases 13 and lips 14 nest as shown. One of the discs 17 is laid on top and the other disc 17 lies beneath the handles 10, as shown. Before the discs are added, a rubber band 26 is stretched around the handles 10 and secured in the grooves 16 thus locking the two handles together. After the discs have been added, another rubber band 27 is passed around the package and is secured in place by the notches 21 in the discs.

By this means two complete handles 10 and their discs 17 are neatly and conveniently packaged together. The discs add little to the volume and the assembly can, after sterilization, be enclosed in a sterile plastic bag (not shown). Upon opening the bag one or both handles 10 and discs 17 may be removed, using sterile gloves, assembled as shown in FIG. 5 and screwed into a socket on the lamp, meanwhile observing sterility procedures.

The hexagon shape at the base 13 and lip 14 are preferred because, when lying flat, the handles 10 do not roll.

Dimensions of the handle 10 will be such that it can be grasped conveniently by hand and manipulated. The disc 17 will have a diameter such that it will effectively prevent the manipulating hand or fingers from touching non-sterile hardware above. Typical dimensions are:

Handle 10

Height from base 13 to lip 14—3.9"
Overall height—4.9"
Diameter of handle element 11—1.25"

Diameter (between opposite sides) of base 13 and lip 14—1.6"

Disc 17

Diameter—4.5"
Thickness—0.08"

It will therefore be appreciated that a novel and useful device has been provided which minimizes packaging problems and serves the intended purpose.

I claim:

1. A multi-part handle for attachment to a handle-receiving fitting on a lamp mounted above an operating table, said handle comprising:
    an elongate handle member having a first end segment and a second end segment, extending in opposite directions from disc support structure of said handle member, said second end segment being configured along its entire length to be manually graspable and moved;
    attachment means carried by said first end segment for engaging a said fitting; and
    a disc separate from said handle member and having a central aperture configured to pass over said first end segment and said attachment means, whereby said handle may selectively be assembled or disassembled;
    said disc support structure constituting means for physically preventing said disc from passing to said second end segment when said handle is assembled.

2. A multi-part handle according to claim 1, wherein said disc support structure has a cross-section transverse said handle member configured with respect to said central aperture of said disc to block passage of said disc.

3. A multi-part handle according to claim 2, wherein the perimeter of said disc support structure is configured to resist rolling of said handle member when said handle is disassembled and said handle member is placed on a flat surface.

4. A multi-part handle according to claim 1, which, when assembled, has a largest perimeter parallel the major axis of said handle congruent with the perimeter of said disc.

5. A multi-part handle for attachment to a handle-receiving fitting on a lamp mounted above an operating table, said handle comprising:
    an elongate handle member having a first end segment and a second end segment, said second end segment having a length and diameter suitable to be manually grasped and moved;
    attachment means carried by said first end segment for engaging a said fitting;
    a disc separate from said handle member and having a central aperture configured to pass over said first end segment and said attachment means, whereby said handle may selectively be assembled or disassembled; and
    support means between said first and second end segments for physically preventing said disc from passing to said second end segment when said handle is assembled;
    the outer perimeter of said disc being larger than the outer perimeter of any other portion of the assembled handle.

6. A multi-part handle according to claim 5, wherein said support means comprises structure having a cross-section transverse said handle member configured with respect to said central aperture of said disc to block passage of said disc.

7. A multi-part handle according to claim 6, wherein the perimeter of said structure is configured to resist rolling of said handle member when said handle is disassembled and said handle member is placed on a flat surface.

8. A multi-part handle for attachment to a handle-receiving fitting on a lamp mounted above an operating table, said handle comprising:
    an elongate handle member having a first end segment and a second end segment, extending in opposite directions from disc support structure of said handle member, said second end segment being configured along its entire length to be manually graspable by a hand wrapped therearound and moved;
    attachment means carried by said first end segment for engaging said fitting; and
    a guard disc constituting means for preventing contact of a hand wrapped around the second end segment with a lamp to which the handle is attached, separate from said handle member and having a central aperture configured to pass over said first end segment and said attachment means, whereby said handle may selectively be assembled or disassembled;
    said disc support structure constituting means for physically preventing said disc from passing to said second end segment when said handle is assembled; and
    said engagement of said attachment means and a said fitting preventing said disc from moving substantially from the disc support structure.

9. A multi-part handle according to claim 8 wherein said disc support structure has a cross-section transverse said handle member configured with respect to said central aperture of said disc to block passage of said disc.

10. A multi-part handle according to claim 9 wherein the perimeter of said disc support structure is configured to resist rolling of said handle member when said handle is disassembled and said handle member is placed on a flat surface.

11. A multi-part handle according to claim 8, which, when assembled, has a largest perimeter parallel the major axis of said handle congruent with the perimeter of said disc.

12. A multi-part handle for attachment to a handle-receiving fitting on a lamp mounted above an operating table comprising:
    an elongate handle member having a first end segment and a second end segment, said second end segment having a length and diameter suitable to be manually grasped with the hand wrapped therearound and moved;
    attachment means carried by said first end segment for engaging a said fitting;
    a guard disc separate from said handle member and having a central aperture configured to pass over said first end segment and said attachment means, whereby said handle may selectively be assembled or disassembled; and
    support means between said first and second end segments for physically preventing said disc from passing to said second end segment when said handle is assembled;

said attachment means and said support means being arranged and configured such that engagement of said attachment means and a fitting prevents said disc from moving substantially away from said support means;

the outer perimeter of said disc being larger than the outer perimeter of any other portion of the assembled handle.

13. A multi-part handle according to claim 12, wherein said support means comprises structure having a cross-section transverse said handle member configured with respect to said central aperture of said disc to block passage of said disc.

14. A multi-part handle according to claim 13, wherein the perimeter of said structure is configured to resist rolling of said handle member when said handle is disassembled and said handle member is placed on a flat surface.

15. A package comprising:
a pair of handles positioned adjacent one another, each said handle comprising:
an elongated handle member having an upper end and a lower end, said handle member having a length and diameter suitable to be manually grasped and moved; and
attachment means mounted at said upper end of said handle member for attaching said handle to an overhead lamp; and
a pair of discs arranged parallel to one another and positioned spacedly apart from one another, one of said discs being arranged in an overlying relation to said handles, one of said discs being arranged in an underlying relation to said handle members; each said disc being detachably mountable on a respective said handle member, each said disc having a center opening configured to be fitted over an encircle an upper end of said respective handle member, each said disc being readily separable from its respective said handle member; and
tie means for holding said discs together positioned about said discs to retain said discs together.

16. The package of claim 15 wherein each said handle member is formed with at least one recess between its lower end, and its upper end, said package further including a first tie member surrounding said handle members and positioned within said handle member recesses to retain said handle members in physical association one with another; and
wherein said discs are formed with recesses on opposite sides thereof, one said disc being positioned on one face of said pair of handle members and the other said disc being positioned on the opposite face of said pair of handle members, said package further including a second tie member surrounding said discs positioned and retained within said disc recesses to retain said discs in physical association with said handle members.

17. The package of claim 15 wherein said handle members are arranged parallel and adjacent to one another, and said discs are positioned contiguous said handle members.

18. A package comprising:
a pair of disassembled handles, each said handle being adapted for manipulating a lamp above an operating table, and each said handle comprising:
an elongate handle member having an upper end, a lower end, and an outwardly projecting support member between said ends, the lower end of said handle member being configured to be grasped by a user,
attachment means mounted on said upper end for attaching said handle member to a lamp above an operating table, and
a disc for detachably mounting on said handle member and being supported when placed thereon by said projecting support member; and
means for holding said handles together in a compact arrangement with said elongate handle members positioned parallel and adjacent one another and with said discs detached from said elongate handle members and parallel one another and said elongate handle members.

19. The package of claim 18 wherein each said handle member of said first handle and said second handle defines a circumferential groove therein, said package further including a first rubber band positioned within each of said grooves for detachably locking paid pair of handles together.

20. The package of claim 19, wherein each of said discs defines a pair of notches therein, said package further including a second rubber band positioned within said notches of said discs of said first handle member and said second handle member to detachably retain said discs in association with said handle members.

21. The package of claim 20 wherein said notches in each said disc are positioned diametrically opposite one another in each said disc.

22. A package comprising:
a pair of handles positioned adjacent and parallel to one another, each said handle comprising:
an elongated handle section having an upper end and a lower end, said handle section having a length and a diameter suitable to be manually grasped and moved;
an attachment means including a plurality of male threads mounted at said upper end of said handle for attaching said handle to an overhead lamp overlying an operating table;
a pair of planar panel members, each having a polygonally-shaped perimeter, one said panel member being mounted on said handle below said attachment means, another said panel member being mounted on said handle's lower end;
wherein each said panel member of each handle overlaps a corresponding panel member of another handle, said polygonal perimeters of each pair of overlapping panel members forming a pair of oppositely positioned, substantially linear support surfaces, said pair of support surfaces formed on said upper ends of said handles being oriented parallel to a pair of support surfaces formed on said lower ends of said handles;
a pair of flat, planar discs arranged parallel one another and positioned spacedly apart from one another, one of said discs being arranged in an overlying relation to said handles, one of said discs being arranged in an underlying relation to said handles, each said disc being detachably mountable on a respective said handle, each said disc having a center opening configured to be fitted over and encircle an upper end of said respective handle section, each said disc being configured to be supportable by a respective said support member, and having an outer diameter dimensioned to prevent inadvertent contact by the hand of a user with non-sterile equipment positioned above each said disc, each said disc being readily separable from its respective said handle;

each said disc defining a pair of recesses therein about a circumference thereof, said recesses being defined on opposing sides of said circumference;

wherein said discs are positioned in a contiguous abutting relationship with said handle-defined support surfaces;

wherein each said handle section is formed with at least one recess between its lower end and its attachment member, said package further including a first tie member surrounding said handles and positioned within said handle recesses to retain said handles in physical association one with another; and wherein said discs are formed with recesses on opposite sides thereof, one said disc being positioned on one face of said pair of handles and the other said disc being positioned on the opposite face of said pair of handles, said package further including a second tie member surrounding said discs positioned and retained within said disc recesses to retain said discs in physical association with said handles.

23. The package of claim 22 wherein said first and second tie members are rubber bands.

24. A package comprising:

a pair of disassembled handles, each said handle being adapted for manipulating a lamp above an operating table, and each said handle comprising:

an elongate handle member having an upper end, a lower end, and an outwardly projecting support member between said ends, the lower end of said handle member being configured to be grasped by a user;

attachment means mounted on said upper end for attaching said handle member to a lamp above an operating table; and a disc for detachably mounting on said handle member and being supported when placed thereon by said projecting support member; and means for holding said handles together in a compact arrangement with said elongate handle members positioned parallel and adjacent one another and with said discs detached from said elongate handle members and parallel one another and said elongate handle members.

* * * * *